United States Patent [19]
Kajihara et al.

[11] Patent Number: 5,753,123
[45] Date of Patent: May 19, 1998

[54] METHOD FOR PURIFYING THROMBOMODULIN

[75] Inventors: Jun-ichi Kajihara, Kobe; Aki Asada, Akashi; Kozue Shibata; Kazuo Katoh, both of Kobe, all of Japan

[73] Assignee: JCR Pharmaceuticals Co., LTD., Hyogo, Japan

[21] Appl. No.: 735,950

[22] Filed: Oct. 23, 1996

[30] Foreign Application Priority Data

Oct. 24, 1995 [JP] Japan ................... 7-300682

[51] Int. Cl.$^6$ .................................. B01D 15/08
[52] U.S. Cl. .................... 210/656; 530/399; 530/412; 530/413; 530/417
[58] Field of Search ............................. 210/635, 656, 210/659, 198.2; 530/399, 412, 413, 417

[56] References Cited

U.S. PATENT DOCUMENTS

| H1148 | 3/1993 | Wakabayashi | 435/13 |
| 5,198,534 | 3/1993 | Steinbuch | 530/381 |
| 5,202,421 | 4/1993 | Kunihira | 530/350 |
| 5,378,816 | 1/1995 | Pungor | 530/412 |

Primary Examiner—Ernest G. Therkorn
Attorney, Agent, or Firm—Jacobson, Price, Holman & Stern, PLLC

[57] ABSTRACT

The present invention permits human urinary thrombomodulin to be purified by a simple and practical procedure, while it enables even a starting material with a lowered content of thrombomodulin to be purified by greater purification rate than the one with a high content of thrombomodulin.

5 Claims, 3 Drawing Sheets

Lot No. 1

Legend:
- - - - - ; Absorbance at a wavelength of 280 nm
───── ; Activity
─ · ─ ; Concentration of phosphoric acid Legend:
- - - - - ; Absorbance at a wavelength of 280 nm
────── ; Activity
─·─·─ ; Concentration of phosphoric acid Lot No. 2

0.3M

Legend:

----- ; Absorbance at a wavelength of 280 nm
——— ; Activity
—·— ; Concentration of phosphoric acid Legend:
Lane 1; M.W. Marker (94, 67, 43, 30, 20.1 kDa)
Lane 2; TM (Lot No. 1) (reducing)
Lane 3; TM (Lot No. 2) (reducing)
Lane 4; TM (Lot No. 1) (non-reducing)
Lane 5; TM (Lot No. 2) (non-reducing)

METHOD FOR PURIFYING THROMBOMODULIN

The present invention relates to a method for purifying through concentration thrombomodulin contained in human urine. Thrombomodulin is an anticoagulant and is expected to find application as a prophylactic and therapeutic agent against diseases being associated with abnormalities in blood coagulation capability.

BACKGROUND OF THE INVENTION

Thrombomodulin (hereinafter referred to briefly as "TM"), which is a high-affinity thrombin-receptor being present on the angioendothelial cells, was discovered by N. L. Esmon et al. (J. Biol. Chem., 257: 859–864, 1982) as a protein being capable of promoting the activation of protein C. TM binds to thrombin at a molar ratio of 1:1 to thereby activate protein C in the presence of $Ca^{2+}$, while, on the other hand, the TM-bound thrombin loses almost entirely its own coagulation activities, such as fibrinogen-agglutinating activity and platelet activating activity. TM, with its endogenous heparin activity, is also known to promote the thrombin suppression by anti-thrombin III, and is expected to find clinical application as a novel type of drugs.

Human TM was initially purified from the human placenta by H. H. Salem et al. (J. Biol. Chem., 259: 12246–12251, 1984), but the human placenta was not suited as a starting material for the large-scale production of TM (EMBO J. 6: 1891–1897, 1987). Though the genetic structure of human TM was identified by Suzuki et al. (EMBO J. 6: 1891–1897, 1987), furthermore, it is difficult to synthesize TM having the same sugar chains as those of the naturally occurring one, since TM contains lots of sugar chains.

Subsequently, human urinary TM was isolated and purified by Yamamoto et al. (J. Biochem. 113: 433–440, 1993) and D. E. Jackson et al. (Eur. J. Biochem. 221: 1079–1087, 1994), demonstrating that human urine is suitable as a starting material for isolating the naturally occurring type of TM.

Referring to the method for purifying TM from urine, Yamamoto et al. produced purified TM by use of QAE Sephadex, anti-TM monoclonal antibody column, affinity column in which thrombin was used as a ligand, and Sephadex G-200, but because the method requires preparation of the monoclonal antibody, its procedure is therefore complicated and troublesome. D. E. Jackson et al. purified TM by the combined use of DEAE Sepharose, affinity column with thrombin employed as a ligand and reverse-phase HPLC, wherein the method encountered the problems in that the purification yield attainable by reverse-phase HPLC is very poor and that HPLC is not suited for large-scale purification. Furthermore, Aoki et al. (Japanese Patent Application Laid-Open No. Sho-63-30423) and Kunihiro et al. (Japanese Patent Application Laid-Open No. Sho-63-218399) reported that TM was purified from fresh urine by ion exchange chromatography, thrombin-bound affinity column and gel permeation. From the inventors' experience, nevertheless, it has been learnt that the content of TM in urine is not always constant, while in the case of lowered TM contents, especially, such method often does not work satisfactorily. Consequently, there is strongly demanded the development of a practically expedient and efficient purification means that can be applied even when urinary TM contents are low.

SUMMARY OF THE INVENTION

In view of the above, the inventors investigated into a purification means which would be able to permit TM with an enhanced degree of purity to be produced, irrespective of the magnitude of TM contents in urine.

In order to solve the above-mentioned problem, the present inventors conducted repeatedly extensive investigation and as a result, found that adsorption chromatography with hydroxyapatite used as an adsorbent is highly effective for the purification of thrombomodulin, resulting in completion of the present invention.

The present invention relates to a method for purifying human urinary thrombomodulin, which comprises purifying human urinary thrombomodulin by employing adsorption chromatography with hydroxyapatite used as an adsorbent.

DESCRIPTION OF THE PREFERRED EMBODIMENTS

Referring to a material containing human urinary thrombomodulin which is a starting material in the method of the present invention, there may be used, for example, raw human urine as such or after being concentrated by fractionation with ammonium sulfate, desirably preliminarily purified human urine obtained by means of anion-exchange chromatography, thrombin-bound affinity chromatography, etc., if possible, though no particular limitation is posed.

With specific reference to hydroxyapatite, there may be utilized any commercially available products (for example, those manufactured by Seikagaku Kogyo K. K. of Japan and Wako Pure Chemicals Co. of Japan).

In cases where a starting material is available in small quantities, it is possible to employ HPLC column for fractionation or analytical uses, such as TSK gel HA-1000 (manufactured by Tosoh Inc. of Japan) and KBC columns (manufactured by Kohken Co., Ltd. of Japan).

A column is packed with hydroxyapatite and then equilibrated with a 1 to 30 mM, preferably 5 to 10 mM phosphate buffer adjusted at pH 5 to 8, preferably pH 6 to 7, whereby it is effective to add salts, such as calcium chloride, sodium chloride, potassium chloride and magnesium chloride, to the equilibrating solution used, with calcium chloride of less than 1 mM in concentration being particularly preferably utilized.

Then, a starting material is applied to the thus buffer-replaced column, followed by washing thoroughly with the same buffer. After the effluent shows fully decreased absorption at a wavelength of 280 nm, elution is conducted with phosphoric acid at a linear concentration gradient, whereby a concentration gradient in the range of 5 to 300 mM is suited for the purification of TM. In the step of elution, TM is eluted in the first place (the phosphoric acid concentration is in the region of 50 to 100 mM), with impurities being eluted subsequently. In cases where an open column is used, meanwhile, such open column can desirably be shaped in the long and narrow form to achieve improved separation. When impurities are still detected even after completion of this step, the final, ultimate purification can be carried out by means of gel permeation, etc. The procedure of adsorption chromatography with use of hydroxyapatite according to the present invention offers the characteristic feature that even when a starting material with lowered specific activity is applied to such chromatographic procedure, there can always be produced the purified product with the same degree of purity as in the case of the ones with high specific activity.

The method of the present invention can be used in combination with other chromatographic procedures, such as ion exchange chromatography, thrombin-bound affinity chromatography and gel filtration chromatography so as to purify human urinary thrombomodulin.

In each purification step, the specific activity of TM can be assayed by the following procedure: 30 µl of Buffer A (20 mM Tris-HCl buffer (pH 7.5) containing 0.1M sodium chloride and 3.5 mM calcium chloride), 10 µl of a human Protein C solution [a solution being prepared with Buffer B (a solution of 0.1% BSA in Buffer A) to a concentration of 100 µg/ml], 10 µl each of a sample and the standard sample are mixed, and 50 µl of a human thrombin solution (a solution being prepared with Buffer B to a concentration of 4 U/ml) is added to the mixture solution, followed by incubation at 37° C. for 30 min. Then, 150 µl of a human antithrombin III solution [a solution being prepared with Buffer C (a solution being prepared with 50 mM tris-HCl solution (pH 7.5) containing 0.1M sodium chloride and 1 mM calcium chloride) to a concentration of 50 µg/ml] and 50 µl of a heparin solution (a solution being prepared with Buffer C to a concentration of 2 U/ml) are added to the reaction solution, followed by incubation at 37° C. for 15 min. 600 ml of a substrate solution {a solution of 25 mg of Test Zyme S-2366 (produced by Daiichi Kagaku Inc. of Japan) in 23.19 ml of Buffer C} is added to the solution, followed by incubation at 37° C. for 20 min, and then, the reaction is stopped by adding 100 µl of a 50% acetic acid solution. The reaction solution is subjected to measurement of absorption at a wavelength of 405 nm to calculate a TM content in the sample on the basis of the absorption measurements obtained with the standard samples (solutions of TM originated from rabbit lungs diluted with Buffer B to concentrations of 2, 5, 10, 20 and 40 mU/ml, respectively, are used as the standard sample).

As may be evident from the above, the present invention, by use of the easy-to-operate procedure of adsorption chromatography, permits not only human urinary thrombomodulin to be concentrated and purified by raised purification rate but also even a starting material with lowered specific activity of thrombomodulin to be purified by greater purification rate than the ones with high specific activity.

BRIEF DESCRIPTION OF THE DRAWINGS

Below described are the examples of the method of the present invention, but this invention is not intended to be limited to the below-described examples, wherein in the attached drawings.

EXAMPLE 1

Figure 1:
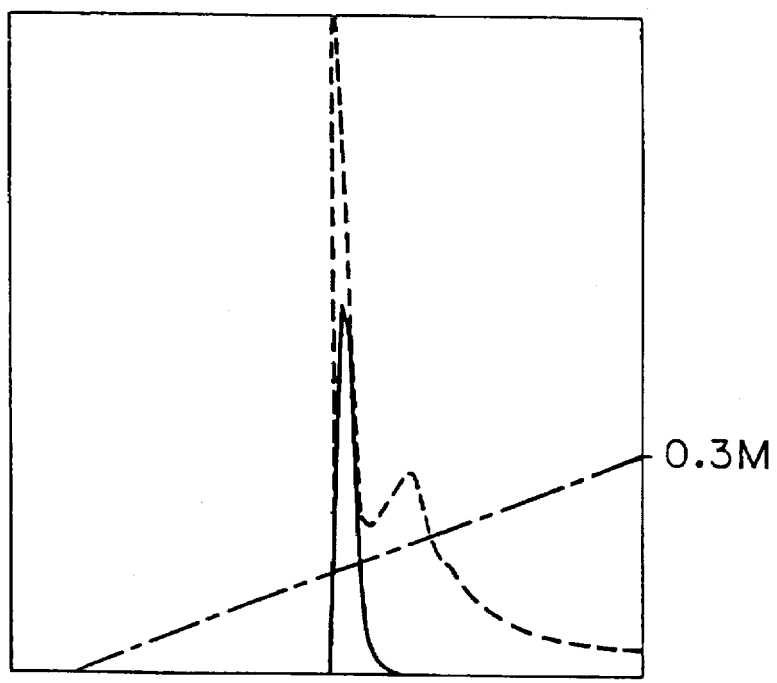
FIG. 1 is an elution patter of thrombomodulin obtained in Example 1 when a starting material (Lot No. 1) containing human urinary thrombomodulin as adsorbed on a hydroxyapatite column was eluted with a linear concentration gradient of sodium phosphate.
Figure 2:
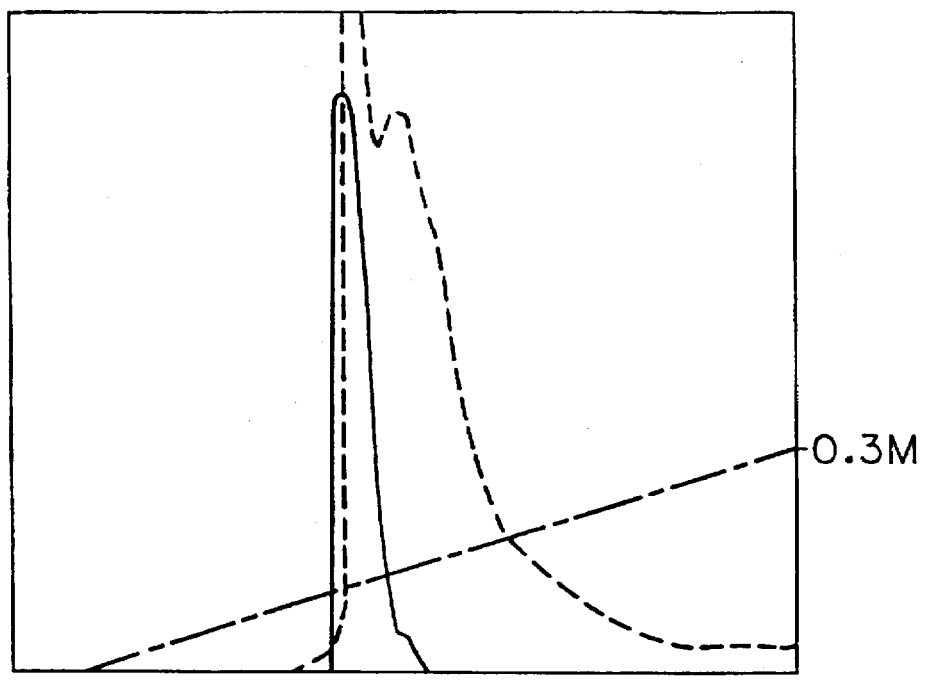
FIG. 2 is an elution pattern of thrombomodulin obtained in Example 2 when the same procedure was conducted with a starting material (Lot No. 2).
Figure 3:
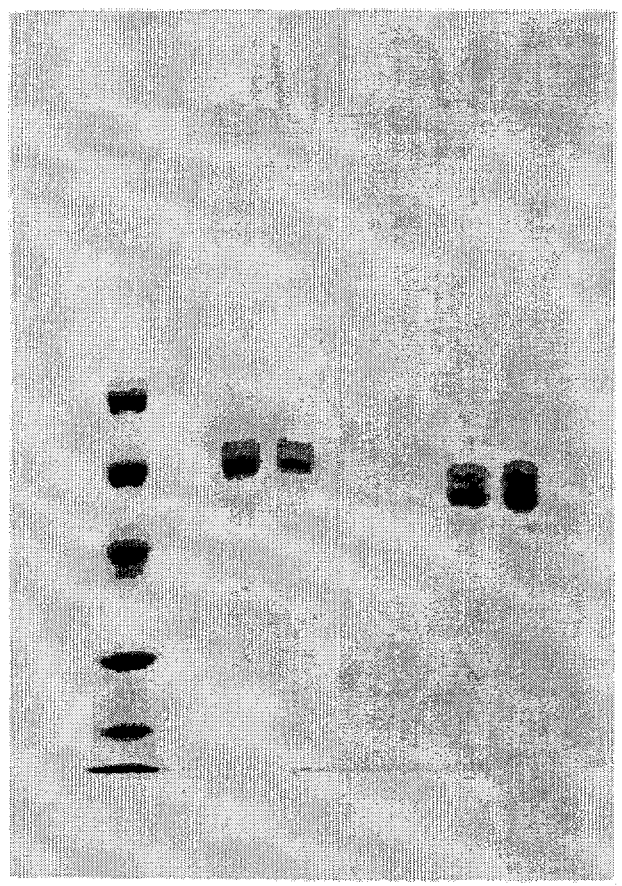
FIG. 3 is a photograph showing the results of SDS polyacrylamide gel electrophoresis under reducing and non-reducing conditions with the purified human urinary thrombomodulin obtained in Example 1.

Outlined below are the purification results obtained with two different lots each of 2000 liters of human urine. A 2,000-liters volume of fresh human urine was adjusted to pH 5.5 and admixed with a 0.5% chitosan solution (w/v) serving as an adsorbent, followed by stirring. The solution mixture was maintained at pH 5.5 for 30 min, filtered, washed with water and suspended in a 5% ammonium sulfate solution (pH 10.5), followed by stirring at room temperature for 1 hour. After the suspension was filtered, followed by washing to elute the adsorbed component, fractionation with 60% ammonium sulfate was effected, and the precipitate was recovered by filtration. The separated precipitate was dissolved in 20 mM Tris-HCl buffer (pH 8.0), and the solution was dialyzed against the same buffer, followed by application onto a column of DEAE-Toyopearl 650M (the resin amount of 1.2 liters; measuring 115 by 11 cm) (manufactured by Tosoh Inc. of Japan) equilibrated in advance with the same buffer. The column was washed with the same buffer, and elution was conducted with the same buffer containing 0.3M sodium chloride. The elution fractions were pooled and diluted 3-fold with 20 mM Tris-HCl buffer (pH 8.0), and the solution was admixed with calcium chloride to a final concentration of 5 mM. The mixture was applied to a DIP-thrombin bound Sepharose column (the resin amount of 40 ml; measuring 2.5 by 8 cm) equilibrated in advance with 20 mM Tris-HCl buffer (pH 8.0) containing 0.1M sodium chloride and 5 mM calcium chloride, and after the column was washed with the same buffer, elution was conducted with 20 mM Tris-HCl buffer (pH 8.0) containing 2M sodium chloride and 10 mM EDTA. The elution fractions were dialyzed against 5 mM sodium-phosphate buffer (pH 6.8) containing 0.4 mM calcium chloride and 0.9% sodium chloride and applied to a column of hydroxyapatite (the adsorbent amount of 20 ml; measuring 1.0 by 25 cm) (manufactured by Seikagaku Kogyo K. K. of Japan) equilibrated in advance with the same buffer. The column was washed with the same buffer, and elution was conducted with a linear concentration gradient of sodium phosphate from 5 to 300 mM, whereby the TM activity was firstly eluted as a sharp peak, as illustrated in FIG. 1 (Lot No. 1) and FIG. 2 (Lot No. 2), with impurities being eluted subsequently. The active fraction was concentrated, and the concentrate was applied onto a column of Sephacryl S-300 (the resin amount of 80 ml; measuring 1.5 cm by 90 cm) (manufactured by Pharmacia Co. of Sweden) equilibrated in advance with 25 mM sodium-phosphate buffer (pH 7.0) containing 0.9% sodium chloride, followed by elution with the same buffer. Tabulated in Table 1 are the results after purification was carried out twice, which indicates that even purification of a starting material exhibiting low specific activity before hydroxyapatite-chromatography was able to provide the purified product with a satisfactorily high degree of specific activity. FIG. 3 illustrates the results of SDS polyacrylamide gel electrophoresis of the final-purified product under reducing and non-reducing conditions, and the figure reveals two neighboring bands (in the neighborhood of 70,000 in molecular weight under reducing conditions) characteristic to TM observed in both of the two lots of the starting material.

TABLE 1

|  | Total activity, U | Yield % | Specific activity, U/mg | Purification rate |
| --- | --- | --- | --- | --- |
| Before hydroxyapatite-chromatography (Lot No. 1) | 5,556 | 100 | 446.3 | 1.0 |
| After hydroxyapatite-chromatography (Lot No. 1) | 4,483 | 81 | 1,306.9 | 2.9 |

TABLE 1-continued

|  | Total activity, U | Yield % | Specific activity, U/mg | Purification rate |
|---|---|---|---|---|
| Before hydroxyapatite-chromatography (Lot No. 1) | 3,071 | 100 | 28.7 | 1.0 |
| After hydroxyapatite-chromatography (Lot No. 1) | 2,565 | 84 | 674.6 | 23.5 |

EXAMPLE 2

In order to confirm that the purified products each consist of TM, furthermore, investigation was conducted to identify the amino acid composition and N-terminal amino acid sequence. The amino acid composition was analyzed by use of an amino-acid analysis device (manufactured by Beckmann Co. of USA) with a hydrolysate with 6N hydrochloric acid, while the N-terminal amino acid sequence was analyzed with Protein Sequencer 473A (manufactured by Applied Bio-System Co. of USA). The results of amino acid analysis are tabulated in Table 2, with the identified N-terminal amino acid sequence being shown below:
N-Terminal amino acid sequence:

Ala-Pro-Ala-Glu-Pro-=Gln-Pro-Gly-Gly-SEr-Gln-

TABLE 2

|  | Purified TM | Ref. |
|---|---|---|
| Asx | 47.0 | 47 |
| Thr | 18.2 | 19 |
| Ser | 23.2 | 24 |
| Glx | 55.1 | 50 |
| Pro | 49.6 | 43 |
| Gly | 50.8 | 46 |
| Ala | 52.7 | 52 |
| Cys | N.D. | 46 |
| Val | 24.6 | 25 |
| Met | 4.9 | 4 |

TABLE 2-continued

|  | Purified TM | Ref. |
|---|---|---|
| Ile | 11.3 | 13 |
| Leu | 34.0 | 32 |
| Tyr | 9.5 | 10 |
| Phe | 16.5 | 16 |
| Lys | 3.0 | 3 |
| His | 11.0 | 12 |
| Arg | 17.2 | 20 |
| Trp | N.D. | 6 |

Notes: N.D. stands for "not detected".
Values in Ref. designate those as calculated from the amino acid sequence of the portion of from Ala 1 to Asp 468 of TM.
Asx stands for (Asp + Asn), while Glx for (Glu + Gln).

We claim:

1. A method for purifying thrombomodulin, which comprises purifying human urinary thrombomodulin by employing adsorption chromatography with hydroxyapatite being used as an adsorbent.

2. A method as claimed in claim 1, wherein purification is conducted solely or in combination by either procedures of ion exchange chromatography, thrombin-bound affinity chromatography and gel permeation chromatography.

3. A method for purifying thrombomodulin, which comprises pouring a starting material containing human urinary thrombomodulin into a column packed with hydroxyapatite to adsorb thrombomodulin, followed by desorption from hydroxyapatite.

4. A method as claimed in claim 3, wherein a starting material containing thrombomodulin is raw human urine, its concentrate obtained through fractionation with ammonium sulfate or its preliminarily purified material obtained by anion exchange chromatography or thrombin-bound affinity chromatography.

5. A method as claimed in, claim 3, wherein adsorption is conducted at pH 5 to 8, while desorption is carried out with a concentration gradient of phosphoric acid.

* * * * *